United States Patent [19]
Ponsati Obiols et al.

[11] Patent Number: 5,880,299
[45] Date of Patent: Mar. 9, 1999

[54] ESTERQUATS

[75] Inventors: Oriol Ponsati Obiols, Barcelona; Nuria Bonastre, Barberá del Vallés; Joaquim Bigorra Llosas, Sabadell, all of Spain

[73] Assignee: Henkel Corporation, Gulph Mills, Pa.

[21] Appl. No.: 736,094

[22] Filed: Oct. 24, 1996

[30]  Foreign Application Priority Data

Oct. 26, 1995 [DE] Germany ............... 195 39 846.7

[51] Int. Cl.$^6$ ................................ C07C 101/00
[52] U.S. Cl. ............ 554/109; 554/103; 554/108; 554/114; 564/281; 564/291; 564/292; 564/296
[58] Field of Search ............... 554/103, 108, 554/109, 114; 564/281, 291, 292, 296

[56]  References Cited

U.S. PATENT DOCUMENTS

| | | | |
|---|---|---|---|
| 3,547,828 | 12/1970 | Mansfield et al. | 252/351 |
| 3,707,535 | 12/1972 | Lew | 260/210 |
| 3,772,269 | 11/1973 | Lew | 260/210 |
| 3,839,318 | 10/1974 | Mansfield | 260/210 |
| 4,172,887 | 10/1979 | Vanlerberghe et al. | 424/70 |
| 4,349,669 | 9/1982 | Klahr et al. | 536/127 |
| 5,349,106 | 9/1994 | Behler et al. | 564/282 |

FOREIGN PATENT DOCUMENTS

| | | |
|---|---|---|
| 077 167 | 4/1983 | European Pat. Off. . |
| 2 252 840 | 8/1975 | France . |
| 1 165 574 | 8/1960 | Germany . |
| 1 943 689 | 3/1970 | Germany . |
| 20 36 472 | 2/1971 | Germany . |
| 20 24 051 | 12/1971 | Germany . |
| 30 01 064 | 7/1981 | Germany . |
| 38 16 200 | 11/1988 | Germany . |
| 40 26 184 | 2/1992 | Germany . |
| 43 08 792 | 4/1994 | Germany . |
| 43 08 794 | 4/1994 | Germany . |
| 42 43 547 | 6/1994 | Germany . |
| 43 35 782 | 7/1994 | Germany . |
| 44 09 322 | 4/1995 | Germany . |
| 43 39 643 | 6/1995 | Germany . |
| WO 91/01295 | 2/1991 | WIPO . |

OTHER PUBLICATIONS

C.R. CED–Congress, Barcelona, 1992, p. 167.
Tens.Surf.Det, 30, 1993, p. 186.
Tens.Surf.Det, 30, 1993, p. 394.
J.Am.Oil.Chem.Soc., 71, 1994, p. 97.
Surfactants in Consumer Products, Springer–Verlag, Berlin, 1987, pp. 54 to 124.
Katalysatoren, Tenside und Mineralöladditive, Thieme Verlag Stutgart, 1978, pp. 123–217.
Kosmetische Färbemittel of the Farbstoffkommission der Deutschen Forschungsgemeinschaft, 1984, pp. 81–106.

*Primary Examiner*—Gary Geist
*Assistant Examiner*—Deborah D. Carr
*Attorney, Agent, or Firm*—Ernest G. Szoke; Wayne C. Jaeschke; Real J. Grandmaison

[57]  ABSTRACT

The invention relates to new esterquats which are obtained by reacting trialkanolamines with a mixture of fatty acids and dicarboxylic acids and quaternizing the resulting esters in known manner, optionally after alkoxylation. Cationic surfactants are obtained which show particularly high ecotoxicological compatibility, provide synthetic and natural fibers with a pleasant feel and, at the same time, reduce electrostatic charging between the filaments.

20 Claims, No Drawings

ESTERQUATS

BACKGROUND OF THE INVENTION

1. Field of the Invention

This invention relates to new esterquats which are obtained by reacting trialkanolamines with fatty acids and dicarboxylic acids and quaternizing the resulting esters—optionally after alkoxylation—in known manner.

2. Discussion of Related Art

"Esterquats" are generally understood to be quaternized fatty acid triethanolamine ester salts which are broadly suitable both for softening fibers and for conditioning hair. In recent years, these substances have significantly displaced conventional quaternary ammonium compounds, for example distearyl dimethyl ammonium chloride, from the market by virtue of their better ecotoxicological compatibility. Reviews of this subject have been published, for example, by O. Ponsati in C. R. CED-Congress, Barcelona, 1992, page 167, by R. Puchta et al. in Tens. Surf. Det. 30, 186 (1993), by M. Brock in Tens. Surf. Det. 30, 394 (1993) and by R. Lagerman et al. in J. Am. Oil. Chem. Soc., 71, 97 (1994).

Although known esterquats have very favorable performance properties and show satisfactory biodegradability and high compatibility with the skin, consumers are still demanding improved product properties.

Accordingly, the problem addressed by the present invention was to provide new esterquat types which would be distinguished by further improved ecotoxocological compatibility and which, at the same time, would exhibit favorable conditioning and antistatic behavior.

DESCRIPTION OF THE INVENTION

The present invention relates to esterquats which are obtained by reacting trialkanolamines with a mixture of fatty acids and dicarboxylic acids and quaternizing the resulting esters in known manner, optionally after alkoxylation.

The esterification of trialkanolamines with a mixture of fatty acids and dicarboxylic acids gives new cationic or amphoteric esterquat surfactants which are surprisingly distinguished from known products not only by particularly favorable ecotoxicological compatibility, but also by excellent hair conditioning and fiber softening properties and by a reduction in electrostatic charging between fiber filaments.

The present invention also relates to a process for the production of esterquats in which trialkanolamines are reacted with a mixture of fatty acids and dicarboxylic acids and the resulting esters are quaternized in known manner, optionally after alkoxylation.

Trialkanolamines

Examples of trialkanolamines which may be used as central nitrogen compounds in accordance with the invention are, primarily, triethanolamine and addition products of 1 to 10 moles and preferably 2 to 5 moles of ethylene oxide with these compounds.

Fatty acids

Fatty acids in the context of the invention are understood to be aliphatic carboxylic acids corresponding to formula (I):

  R'CO—OH    (I)

in which $R^1CO$ is an aliphatic, linear or branched acyl radical containing 6 to 22 carbon atoms and 0 and/or 1, 2 or 3 double bonds. Typical examples are caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms, for example coconut oil, palm oil, palm kernel oil or tallow fatty acids, preferably in hydrogenated or partially hydrogenated form, are preferred.

Dicarboxylic acids

Dicarboxylic acids suitable for use as starting materials in accordance with the invention correspond to formula (II):

  HOOC—[X]—COOH    (II)

in which X is an optionally hydroxysubstituted alkylene group containing 1 to carbon atoms. Typical examples are succinic acid, maleic acid, glutaric acid, 1,12-dodecanedioic acid and, in particular, adipic acid.

Esterification

The fatty acids and the dicarboxylic acids may be used in a molar ratio of 1:10 to 10:1. However, it has proved to be of advantage to adjust a molar ratio of 1:4 to 1:6. The trialkanolamines on the one hand and the acids—i.e. fatty acids and dicarboxylic acids together—on the other hand may be used in a molar ratio of 1:1.3 to 1:2.4. A molar ratio of trialkanolamine to acids of 1:1.4 to 1:1.8 has proved to be optimal.

The esterification may be carried out in known manner, for example as described in International patent application WO 91/01295 (Henkel). In one advantageous embodiment, it is carried out at temperatures of 120° to 220° C. and, more particularly, 130° to 170° C. under pressures of 0.01 to 1 bar. Suitable catalysts are hypophosphorous acids and alkali metal salts thereof, preferably sodium hypophosphite, which may be used in quantities of 0.01 to 0.1% by weight and preferably in quantities of 0.05 to 0.07% by weight, based on the starting materials. In the interests of particularly high color quality and stability, it has proved to be of advantage to use alkali metal and/or alkaline earth metal borohydrides, for example potassium, magnesium and, in particular, sodium borohydride, as co-catalysts. The co-catalysts are normally used in quantities of 50 to 1000 ppm and, more particularly in quantities of 100 to 500 ppm, again based on the starting materials. Corresponding processes are also the subject of DE-C1 43 08 792 and DE-C1 44 09 322 (Henkel) to which reference is hereby specifically made. Mixtures of the fatty acids and dicarboxylic acids may be used or, alternatively, the esterification may be carried out with the two components in successive steps.

Alkoxylation

Esterquats containing polyalkylene oxide may be produced by two methods. First, ethoxylated trialkanolamines may be used. This has the advantage that the distribution of alkylene oxide in the resulting esterquat is substantially the same in regard to the three OH groups of the amine. However, it also has the disadvantage that the esterification reaction is more difficult to carry out on steric grounds. Accordingly, the preferred method is to alkoxylate the ester before quaternization. This may be done in known manner, i.e. in the presence of basic catalysts and at elevated temperatures. Suitable catalysts are, for example, alkali metal and alkaline earth metal hydroxides and alcoholates, preferably sodium hydroxide and, more preferably, sodium methanolate. The catalysts are normally used in quantities of 0.5 to 5% by weight and preferably in quantities of 1 to 3% by weight, based on the starting materials. Where these catalysts are used, free hydroxyl groups are primarily alkoxylated. However, if calcined hydrotalcites or hydrotalcites hydrophobicized with fatty acids are used as catalysts, the alkylene oxides are also inserted into the ester bonds. This method is preferred where the required alkylene oxide distribution approaches that obtained where alkoxylated trialkanolamines are used. Ethylene and propylene oxide and mixtures thereof (random or block distribution) may be used as alkylene oxides. The reaction is normally carried out at temperatures in the range from 100° to 180° C. The incorporation of, on average, 1 to 10 moles of alkylene oxide per mole of ester increases the hydrophilicity of the esterquat, improves solubility and reduces reactivity to anionic surfactants.

Quaternization and alkylating agents

The quaternization of the fatty acid/dicarboxylic acid trialkanolamine esters may be carried out in known manner. Although the reaction with the alkylating agents may also be carried out in the absence of solvents, it is advisable to use at least small quantities of water or lower alcohols, preferably isopropyl alcohol, for the production of concentrates which have a solids content of at least 80% by weight and, more particularly, at least 90% by weight.

Suitable alkylating agents are alkyl halides such as, for example, methyl chloride, dialkyl sulfates, such as dimethyl sulfate or diethyl sulfate for example, or dialkyl carbonates, such as dimethyl carbonate or diethyl carbonate for example.

The esters and the alkylating agents are normally used in a molar ratio of 1:0.95 to 1:1.05, i.e. in a substantially stoichiometric ratio. The reaction temperature is usually in the range from 40° to 80° C. and, more particularly, in the range from 50° to 60° C. After the reaction, it is advisable to destroy unreacted alkylating agent by addition of, for example, ammonia, an (alkanol)amine, an amino acid or an oligopeptide, as described for example in DE-A140 26 184 (Henkel).

Dispersants and emulsifiers

The quaternization is normally carried out either in the absence of water or in the presence of small quantities of a solvent (for example isopropyl alcohol). However, depending on the application envisaged for the esterquats, it can be of advantage to incorporate a future dispersant or emulsifier in the reaction product, i.e. to dispense with the actual solvent of which the function is of course merely to produce a liquid phase, and to carry out the quaternization in the presence of the dispersant/emulsifier as solvent. A corresponding process is described, for example, in DE-C1 43 08 794, DE-C1 43 35 782 and DE-C1 43 39 643 (Henkel).

Suitable dispersants and/or emulsifiers are, for example, fatty alcohols. Typical representatives are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fate and oils or aldehydes from Roelen's oxosynthesis and as monomer fraction in the dimerization of unsaturated fatty alcohols. Technical fatty alcohols containing 12 to 18 carbon atoms, for example coconut oil, palm oil, palm kernel oil or tallow fatty alcohol are preferred.

Other suitable dispersants and/or emulsifiers are polyols of which typical representatives are glycerol;

alkylene glycols such as, for example, ethylene glycol, diethylene glycol, propylene glycol;

technical oligoglycerol mixtures with a degree of autocondensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, more especially those containing 1 to 8 carbon atoms in the alkyl group, for example methyl and butyl glucoside;

sugar alcohols containing 5 to 12 carbon atoms, for example sorbitol or mannitol;

sugars containing 5 to 12 carbon atoms, for example glucose or sucrose;

aminosugars, for example glucamine.

Another group of suitable dispersants and/or emulsifiers are partial glycerides, for example monoglycerides and/or diglycerides, and anionic and nonionic surfactants. Among the nonionic surfactants, it is particularly preferred to use alkyl oligoglucosides, fatty acid-N-alkyl glucamides and/or adducts of, on average, 1 to 50 moles of ethylene oxide with the fatty alcohols mentioned above. The ratio by weight of ester to dispersant/emulsifier may be in the range from 30:70 to 70:30.

Surfactants

The esterquats according to the invention may be used together with other anionic, nonionic, cationic and/or amphoteric surfactants. On account of the problem of adduct formation between cationic and anionic surfactants, mixtures of the esterquats with nonionic, amphoteric and zwitterionic surfactants are of course preferred. However, esterquats, especially those containing polyoxyalkylene groups, show comparatively greatly reduced reactivity to anionic surfactants so that the problem of salt formation and/or inactivation hardly arises in practice.

Typical examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein/fatty acid condensates (more particularly wheat-based vegetable products) and alkyl(ether) phosphates. If the anionic surfactants contain polyglycol ether chains, they may have a conventional homolog distribution although they preferably have a narrow-range homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides, protein hydrolyzates (more particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Typical examples of cationic surfactants are quaternary ammonium compounds and esterquats, more particularly quaternized fatty acid trialkanolamine ester salts.

Typical examples of amphoteric or zwitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. From the applicational point of view, mixtures of esterquats with the surfactants mentioned above in a ratio by weight of 10:90 to 90:10 are preferred. Particularly advantageous properties are obtained with combinations of esterquats with alkyl oligoglucosides, fatty acid-N-alkyl glucamides and/or betaines.

Commercial Applications

The esterquats according to the invention have excellent conditioning properties, are high-foaming and highly detersive where a betaine structure is present, reduce electrostatic charging between synthetic and natural fibers, including keratin fibers, as cationic surfactants and are distinguished by particularly favorable ecotoxicological compatibility.

Accordingly, the present invention also relates to their use for the production of surface-active formulations, for example laundry detergents, dishwashing detergents, cleaners and conditioners and, preferably, hair-care and body-care formulations, in which they may be present in quantities of 1 to 50% by weight and preferably 3 to 35% by weight, based on the formulation.

Hair-care and body-care formulations

The hair-care and body-care formulations, for example hair shampoos, hair lotions, shower gels or foam baths, may also contain oils, emulsifiers, superfatting agents, thickeners, cationic polymers, silicone compounds, biogenic agents, film-formers, preservatives, dyes and fragrances as further additives and auxiliaries.

Suitable oils are, for example, Guerbet alcohols based on fatty alcohols containing 6 to 18 and preferably 8 to 10 carbon atoms, esters of linear $C_{6-20}$ fatty acids with linear $C_{6-2}$ fatty alcohols, esters of branched $C_{6-3}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Nonionic, ampholytic and/or zwitterionic surface-active compounds distinguished by a lipophilic, preferably linear, alkyl or alkenyl group and at least one hydrophilic group may be used as emulsifiers or co-emulsifiers. The hydrophilic group may be both an ionic group and a nonionic group. Nonionic emulsifiers contain, for example, a polyol group, a polyalkylene glycol ether group or a combination of a polyol and a polyglycol ether group as the hydrophilic group.

Preferred formulations are those containing nonionic surfactants from at least one of the following groups as o/w emulsifiers: (a1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group; (a2) $C_{12/18}$ fatty acid monoesters and diesters of adducts of 1 to 30 moles of ethylene oxide with glycerol; (a3) glycerol monoesters and diesters and sorbitan monoesters and diesters of saturated and unsaturated fatty acids containing 6 to 22 carbon atoms and ethylene oxide adducts thereof; (a4) alkyl mono- and oligoglycosides containing 8 to 22 carbon atoms in the alkyl group and ethoxylated analogs thereof and (a5) adducts of 15 to 60 moles of ethylene oxide with castor oil and/or hydrogenated castor oil; (a6) polyol esters and, in particular, polyglycerol esters such as, for example, polyglycerol polyricinoleate or polyglycerol poly-12-hydroxystearate. Mixtures of compounds from several of these classes are also suitable. The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051. $C_{8/18}$ alkyl mono- and oligoglycosides, their production and their use as surfactants are known, for example, from U.S. Pat. Nos. 3,839,318, 3,707,535, 3,547,828, DE-OS 19 43 689, DE-OS 20 36 472 and DE-A1 30 01 064 and also from EP-A 0 077 167. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based. In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine.

Suitable w/o emulsifiers are: (b1) adducts of 2 to 15 moles of ethylene oxide with castor oil and/or hydrogenated castor oil; (b2) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose); (b3) trialkyl phosphates; (b4) wool wax alcohols; (b5) polysiloxane/polyalkyl polyether copolymers and corresponding derivatives; (b6) mixed esters of pentaerythritol, fatty acids, citric acid and fatty alcohol according to DE-PS 11 65 574 and (b7) polyalkylene glycols.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lamequat®L, Grünau GmbH), polyethyleneimine, cationic silicone polymers such as, for example, Amidomethicone or Dow Corning, Dow Corning Co., USA, copolymers of adipic acid and dimethylaminohydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable silicone compounds are, for example, dimethyl polysiloxanes, methylphenyl polysiloxanes, cyclic silicones and amino-, fatty-acid-, alcohol-, polyether-, epoxy-, fluorine- and/or alkyl-modified silicone compounds. In the context of the invention, biogenic agents are, for example, plant extracts and vitamin complexes. Conventional film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid or salts thereof and similar compounds. Suitable preservatives are, for example, phenoxyethanol, formaldehyde solution, parabens, pentanediol or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are normally used in concentrations of 0.001 to 0.1% by weight, based on the mixture as a whole.

In all, the auxiliaries and additives may make up 1 to 50 and preferably 5 to 40% by weight of the formulations.

EXAMPLES

I. Production Examples

Example 1

567 g (2.1 moles) of partly hydrogenated palm oil fatty acid, 219 g (1.5 moles) of adipic acid and 0.3 g of hypophosphoric acid were introduced into a stirred reactor and heated to 70° C. under a reduced pressure of 20 mbar. 447 g (3 moles) of triethanolamine were then added dropwise in portions and, at the same time, the temperature was increased to 120° C. After the addition, the reaction mixture was heated to 160° C., the pressure was reduced to 3 mbar and the mixture was stirred under those conditions for 2.5 h until the acid value had fallen to below 5 mg KOH/g. The mixture was then cooled to 60° C., the vacuum was broken by introduction of nitrogen and 0.6 g of hydrogen peroxide was added in the form of a 30% by weight aqueous solution. For the quaternization step, the resulting ester was dissolved in 376 g of isopropyl alcohol and 357 g (2.83 moles) of dimethyl sulfate were added to the resulting solution over a period of 1 hour at such a rate that the temperature did not rise above 65° C. After the addition, the mixture was stirred for another 2.5 h, the total nitrogen content being regularly checked by sampling. The reaction was terminated when a constant total nitrogen content had been reached. A product with a solids content of 80% by weight was obtained.

Example 2

The procedure was as in Example 1, except that 540 g (2 moles) of partly hydrogenated palm oil fatty acid, 146 g (1 mole) of adipic acid, 1 g of hypophosphoric acid and 298 g (2 moles) of triethanolamine were used. The resulting ester was dissolved in 128 g of isopropyl alcohol and quaternized with 237 g (1.88 moles) of dimethyl sulfate. A product with a solids content of 90% by weight was obtained.

Example 3

As in Example 1, the fatty acid/dicarboxylic acid triethanolamine ester obtained as intermediate product was stirred with 100 g of cocofatty alcohol at 45° C. to form a homogeneous mixture. Quaternization was then carried out as described in Example 1, but with no addition of isopropyl alcohol. A beige-colored wax-like mass, which could readily be processed to flakes, was obtained.

Example 4

The procedure was as in Example 3, except that the cocofatty alcohol was replaced by 100 g of a 35% by weight aqueous paste of an alkyl oligoglucoside (Plantaren® APG 2000, Henkel KGaA, Dusseldorf, FRG). A light beige-colored paste was obtained.

Example 5

The procedure was as in Example 3, except that the cocofatty alcohol was replaced by 100 g of a mixture of a cocofatty acid monoglyceride and a tallow alcohol+40 EO adduct (ratio by weight 1:1). A light yellow-colored wax-like mass, which could readily be processed to flakes, was obtained.

Examples 6, 7 and 8

The procedure was as described in Example 1, except that the adipic acid was replaced by quantities of 1.5 mole of succinic acid, glutaric acid and 1,12-dodecanedioic acid, respectively. In all three cases, dark-colored pastes were again obtained.

Examples 9 and 10

The procedure was as in Example 1, except that the dimethyl sulfate was replaced by quantities of 2.8 moles of methyl chloride and diethyl carbonate, respectively. In both cases, dark-colored pastes were again obtained.

Example 11

The procedure was as in Example 1. The crude fatty acid/dicarboxylic acid triethanolamine ester was transferred to an autoclave in which 5 g—corresponding to 2.5% by weight, based on the ester—of sodium methylate were added in the form of a 30% by weight solution in methanol. The autoclave was alternately evacuated and repurged with nitrogen three times, heated to 125° C. and then charged in portions with 44 g (1 mole) of ethylene oxide. After the addition, the reaction mixture was stirred for another 30 minutes, after which the autoclave was cooled and vented. The ethoxylated triethanolamine ester was then quaternized as described in Example 1. A light yellow-colored flowable paste was obtained.

II. Application Examples—Hair Cosmetics

TABLE 1

Application Examples (percentages as % by weight; water + preservative to 100%)

| Product | Component | CTFA Name | Content % |
|---|---|---|---|
| Hair rinse | Emulgade PL ® 1618 | Hexyl Polyglucose (and) Hexadecyl Alcohol | 4.0 |
|  | Nutrilan ® Keratin W | Hydrolyzed Keratin | 2.3 |
|  | Plantaren ® 1200 | Lauryl Polyglucose | 2.0 |
|  | Esterquat | According to Example 1 | 1.0 |
|  | Lameform ® TGI | Polyglyceryl-3-Diisostearate | 1.0 |
|  | Cetiol ® V | Decyl Oleate | 1.0 |
|  | Cutina ® MD | Glyceryl Stearate | 0.5 |
| Hair rinse | Lanette ® O | Cetearyl Alcohol | 2.5 |
|  | Esterquat | According to Example 1 | 1.0 |
|  | Cetiol ® OE | Dicapryl Ether | 1.0 |
|  | Eumulgin ® B2 | Ceteareth-20 | 0.8 |
|  | Cutina ® MD | Glyceryl stearate | 0.5 |
| Hair rinse | Lenette ® O | Cetearyl Alcohol | 2.5 |
|  | Esterquat | According to Example 1 | 1.0 |
|  | Eutanol ® G | Octyldodecanol | 1.0 |
|  | Eumulgin ® B2 | Ceteareth-20 | 0.8 |
|  | Cutina ® MD | Glyceryl Stearate | 0.5 |
| Hair rinse | Lanette ® O | Cetearyl Alcohol | 2.5 |
|  | Nutrilan ® I-50 | Hydrolyzed Collagen | 2.0 |
|  | Esterquat | According to Example 1 | 1.0 |
|  | Lameform ® TGI | Polyglyceryl-3 Diisostearate | 1.0 |
|  | Cetiol ® V | Decyl oleate | 1.0 |
|  | Eumulgin ® B2 | Cetearth-20 | 0.8 |
|  | Cutina ® MD | Glyceryl Stearate | 0.5 |
| Leave-on-hair rinse | Sepigel ® 305 |  | 3.0 |
|  | Nutrilan ® I-50 | Hydrolyzed Collagen | 2.0 |
|  | Esterquat | According to Example 1 | 0.8 |
|  | Plantaren ® 1200 | Lauryl Polyglucose | 0.5 |
|  | Cetiol ® J 600 | Oleyl Erucate | 0.5 |
|  | Copherol ® 1250 | Tocopheryl Acetate | 0.2 |
|  | Ethanol |  | 10.0 |
|  | Glycerol (86%) |  | 5.0 |
| Hair conditioner | Lanette ® O | Cetearyl Alcohol | 3.0 |
|  | Generol ® 122 | Soya sterol | 1.0 |
|  | Esterquat | According to Example 1 | 1.0 |
|  | Eumulgin ® B2 | Ceteareth-20 | 0.8 |
|  | Cutina ® MD | Glyceryl Stearate | 0.5 |

TABLE 19

Application Examples-Hair Cosmetics (continued)

| Product | Component | CTFA Name | Content % |
|---|---|---|---|
| Hair conditioner | Lanette ® O | Cetearyl Alcohol | 2.5 |
|  | Esterquat | According to Example 1 | 1.5 |
|  | Eumulgin ® B2 | Ceteareth-20 | 1.0 |
|  | Generol ® 122 | Soya sterol | 1.0 |
|  | Eutanol ® G | Octyldodecanol | 1.0 |
|  | Cutina ® MD | Glyceryl Stearate | 0.5 |
| Show Bath | Texapon ® K 14 S | Sodium Myreth Sulfate | 38.0 |
|  | Plantaren ® 2000 | Decyl Polyglucose | 7.0 |
|  | Lamesoft ® LMG | Glyceryl Laurate (and) Potassium Cocoyl Hydrol. Collagen | 3.0 |
|  | Arlypon ® F | Laureth-2 | 3.0 |
|  | Esterquat | According to Example 1 | 0.5 |

TABLE 19-continued

Application Examples-Hair Cosmetics (continued)

| Product | Component | CTFA Name | Content % |
|---|---|---|---|
| Foam bath | Texapon ® NSO | Sodium Laureth Sulfate | 38.0 |
| | Plantaren ® 2000 | Decyl Polyglucose | 7.0 |
| | Euperian ® PK 3000 | Glycol Distearate (and) Cocoamidopopyl Betaine | 3.0 |
| | Arlypon ® F | Laureth-2 | 3.0 |
| | Lamesoft ® LMG | Glyceryl Laurate (and) Potassium Cocoyl Hydrol. Collagen | 2.0 |
| | Esterquat | According to Example 1 | 0.5 |
| | Sodium chloride | | 1.5 |
| Shower gel | Texapon ® NSO | Sodium Laureth Sulfate | 25.0 |
| | Texapon ® SB3 | Disodium Laurethsulfosuccinate | 10.0 |
| | Dehyton ® K | Cocoamidopropyl Betaine | 10.0 |
| | Plantaren ® 2000 | Decyl Polyglucose | 6.0 |
| | Euperlan ® PK 3000 | Glycol Distearate (and) Cocoamidopropyl Betaine | 5.0 |
| | Lamesoft ® LMG | Glycol Distearate (and) Cocoamidopropyl Betaine | 4.0 |
| | Cetiol ® HE | PEG-7 Glyceryl Cocoate | 1.0 |
| | Arlypon ® F | Laureth-2 | 1.0 |
| | Esterquat | According to Example 1 | 0.5 |
| Wash lotion | Plantaren ® PS 10 | Sodium Laureth Sulfate (and) Lauryl Polyglucose | 16.0 |
| | Euperlan ® PK 3000 | Glycol Distearate (and) Cocoamidopropyl Betaine | 5.0 |
| | Esterquat | According to Example 1 | 0.5 |
| | Sodium salt | | 1.5 |

TABLE 1C

Application Examples-Hair Cosmetics (continued)

| Product | Component | CTFA Name | Content % |
|---|---|---|---|
| "2 in 1" Shower bath | Texapon ® NSO | Sodium Laureth Sulfate | 20.0 |
| | Dehyton ® K | Cocoamidopropyl Betaine | 20.0 |
| | Plantaren 2000 | Decyl Polyglucose | 5.0 |
| | Nutrilan ® I-50 | Hydrolyzed Collagen | 1.0 |
| | Esterquat | According to Example 1 | 1.0 |
| | Euperlan ® PK 3000 | Glycol Distearate (and) Cocoaidopropyl Betaine | 5.0 |
| | Lytron ® 631 | Sodium Styrene/Acrylate Copol. | 2.0 |
| | Arlpon ® F | Laureth-2 | 0.5 |
| "2 in 1" Shower bath | Plantaren ® PS 10 | Sodium Laureth Sulfate (and) Lauryl Polyglucose | 40.0 |
| | Eumulgin ® B2 | Ceteareth-20 | 1.0 |
| | Eutanol ® G | Octyldodecanol | 3.0 |
| | Lamecreme ® DGE 18 | Polyglyceryl-2-PEG-4 Copolymer | 4.0 |
| | Lytron ® 631 | Sodium Styrene/Acrylate Copolym. | 1.0 |
| | Esterquat | According to Example 1 | 1.0 |
| | Perfume | | 0.5 |
| Shampoo | Texapon ® NSO | Sodium Laureth Sulfate | 25.0 |
| | Plantaren ® 2000 | Decyl Polyglucose | 5.0 |
| | Dehyton ® K | Cocoamidopropyl Betaine | 8.0 |
| | Esterquat | According to Example 1 | 3.0 |
| | Arlypon ® F | Laureth-2 | 1.5 |
| | Eumulgin ® L | PPG-2-Ceteareth-9 | 1.0 |
| | Perfume | | 0.5 |
| Shampoo | Texapon ® N 70 | Sodium Laureth Sulfate | 11.0 |
| | Texapon ® SB 3 | Disodium Laurethsulfosuccinate | 7.0 |
| | Plantaren ® 1200 | Lauryl Polyglucose | 4.0 |
| | Esterquat | According to Example 1 | 1.0 |
| | Nutrilan ® I-50 | Hydrolyzed Collagen | 2.0 |
| | Sodium chloride | | 1.6 |
| Shampoo | Plantaren ® PS 10 | Sodium Laureth Sulfate (and) Lauryl Polyglucose | 16.0 |
| | Esterquat | According to Example 1 | 2.0 |
| | Sodium chloride | | 2.0 |
| Shampoo | Plantaren ® PS 10 | Sodium Laureth Sulfate (and) Lauryl Polyglucose | 17.0 |

TABLE 1C-continued

Application Examples-Hair Cosmetics (continued)

| Product | Component | CTFA Name | Content % |
|---|---|---|---|
| | Nutrilan ® I-50 | Hydrolyzed Collagen | 2.0 |
| | Esterquat | According to Example 1 | 2.0 |
| | Glycerol (86%) | | 1.0 |
| | Euperlan ® PK 900 | Triethylene Glycol Distearate (and) Sodium Laureth Sulfate | 3.0 |
| | Sodium chloride | | 2.0 |

TABLE 1D

Application Examples-Hair Cosmetics (continued)

| Product | Component | CTFA Name | Content % |
|---|---|---|---|
| Shampoo | Texapon ® ALS | Ammonium Laureth Sulfate | 23.0 |
| | Plantaren ® 2000 | Decyl Polyglucose | 4.0 |
| | Dehyton ® K | Cocoamidopropyl Betaine | 7.0 |
| | Esterquat | According to Example 1 | 2.0 |
| | Lamesoft ® 156 | Hydrogenated Tallow Glycerides | 5.0 |
| | Monomuls ® 90-L 12 | Glyceryl Laurate | 1.0 |
| | Sodium chloride | | 3.0 |
| Foam bath | Plantaren ® PS 10 | Sodium Laureth Sulfate (and) Lauryl Polyglucose | 22.0 |
| | Dehyton ® K | Cocoamidopropyl Betaine | 15.0 |
| | Esterquat | According to Example 1 | 3.0 |
| | Cetiol ® HE | PEG-7 Glyceryl Cocoate | 2.0 |
| | Euperlan ® PK 300 | Glycol Distearate (and) Cocoamidopropyl Betaine | 5.0 |
| Foam bath | Texapon ® NSO | Sodium Laureth Sulfate | 30.0 |
| | Dehyton ® K | Cocoamidopropyl Betaine | 10.0 |
| | Plantaren ® 1200 | Lauryl Polyglucose | 10.0 |
| | Lamesoft ® LMG | Glyceryl Laurate (and) Potassium Cocoyl Hydrol. Collagen | 4.0 |
| | Esterquat | According to Example 1 | 2.0 |
| | Gaudin ® AGP | Hydrolyzed Wheat protein | 0.5 |
| Foam bath | Melissa oil | | 5.0 |
| | Eumulgin ® L | PPG-2-Ceteareth-9 | 15.0 |
| | Plantaren ® 2000 | Decyl Polyglucose | 30.0 |
| | Dehyton ® K | Cocoamidopropyl Betaine | 10.0 |
| | Esterquat | According to Example 1 | 4.0 |
| | Propylene glycol | | 4.0 |
| | Arlypon ® F | Laureth-2 | 1.5 |

What is claimed is:

1. The process of preparing esterquats consisting essentially of reacting trialkanolamines with a mixture of fatty acids and dicarboxylic.

2. A process as in claim 1 including alkoxylating said esters prior to said quaternizing step.

3. A process as in claim 1 wherein said trialkanolamines comprise triethanolamine.

4. A process as in claim 1 wherein said fatty acids correspond to formula (I):

   (i)

in which $R^1CO$ is an aliphatic, linear or branched acyl radical containing 6 to 22 carbon atoms and 0, 1, 2 or 3 double bonds.

5. A process as in claim 1 wherein said dicarboxylic acids correspond to formula (II):

   (ii)

in which X is an optionally hydroxysubstituted alkylene group containing 1 to 10 carbon atoms.

6. A process as in claim 1 wherein said mixture of fatty acids and dicarboxylic acids is present in a molar ratio of 1:10 to 10:1.

7. A process as in claim 1 wherein said trialkanolamines and said mixture of fatty acids and dicarboxylic acids are present in a molar ratio of 1:1.3 to 1:2.4, respectively.

8. A process as in claim 1 wherein said esters are formed in the presence of hypophosphorous acid or alkali metal salts thereof.

9. A process as in claim 1 wherein said quaternizing step is conducted with an alkylating agent selected from the group consisting of alkyl halides, dialkyl sulfates and dialkyl carbonates.

10. A process as in claim 1 wherein said quaternizing step is carried out in the presence of dispersants or emulsifiers selected from the group consisting of fatty alcohols, polyols, partial glycerides, anionic surfactants and nonionic surfactants.

11. Esterquats prepared by reacting trialkanolamines with a mixture of fatty acids and dicarboxylic acids and quaternizing the resulting esters.

12. Esterquats as in claim 11 wherein said esters are alkoxylated prior to said quaternizing step.

13. Esterquats as in claim 11 wherein said trialkanolamines comprise triethanolamine.

14. Esterquats as in claim 11 wherein said fatty acids correspond to formula (I):

$$R^1CO{-}OH \qquad (I)$$

in which $R^1CO$ is an aliphatic, linear or branched acyl radical containing 6 to 22 carbon atoms and 0, 1, 2 or 3 double bonds.

15. Esterquats as in claim 11 wherein said dicarboxylic acids correspond to formula (II):

$$HOOC{-}[X]{-}COOH \qquad (II)$$

in which X is an optionally hydroxysubstituted alkylene group containing 1 to 10 carbon atoms.

16. Esterquats as in claim 11 wherein said mixture of fatty acids and dicarboxylic acids is present in a molar ratio of 1.10 to 10: 1.

17. Esterquats as in claim 11 wherein said trialanolamines and said mixture of fatty acids and dicarboxylic acids are present in a molar ratio of 1:1.3 to 1:2.4, respectively.

18. Esterquats as in claim 11 wherein said esters are formed in the presence of hypophosphorous acid or alkali metal salts thereof.

19. Esterquats as in claim 11 wherein said quaternizing step is conducted with an alkylating agent selected from the group consisting of alkyl halides, dialkyl sulfates and dialkyl carbonates.

20. Esterquats as in claim 11 wherein said quaternizing step is carried out in the presence of dispersants or emulsifiers selected from the group consisting of fatty alcohols, polyols, partial glycerides, anionic surfactants and nonionic surfactants.

* * * * *